(12) United States Patent
McKenna (10) Patent No.: US 8,406,865 B2
(45) Date of Patent: Mar. 26, 2013

(54) BIOIMPEDANCE SYSTEM AND SENSOR AND TECHNIQUE FOR USING THE SAME

(75) Inventor: Edward M. McKenna, Boulder, CO (US)

(73) Assignee: Covidien LP, Mansfield, MA (US)

(*) Notice: Subject to any disclaimer, the term of this patent is extended or adjusted under 35 U.S.C. 154(b) by 703 days.

(21) Appl. No.: 12/241,428

(22) Filed: Sep. 30, 2008

(65) Prior Publication Data

US 2010/0081960 A1  Apr. 1, 2010

(51) Int. Cl.
*A61B 5/00* (2006.01)

(52) U.S. Cl. .................... 600/547; 600/310

(58) Field of Classification Search ............ 204/403.01; 340/573.1, 539.12; 600/310, 345, 372, 407, 600/473, 475, 476, 477, 506, 547, 509, 322; 604/361
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,723,554 A | 2/1988 | Oman et al. |
| 4,805,365 A | 2/1989 | Jobsis |
| 4,850,365 A | 7/1989 | Rosenthal |
| 4,860,753 A | 8/1989 | Amerena |
| 4,883,055 A | 11/1989 | Merrick |
| 4,907,594 A | 3/1990 | Muz |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,337,745 A | 8/1994 | Benaron |
| 5,337,937 A | 8/1994 | Blank et al. |
| 5,348,004 A | 9/1994 | Hollub |
| 5,355,880 A | 10/1994 | Thomas et al. |
| 5,377,674 A | 1/1995 | Kuestner |
| 5,499,627 A | 3/1996 | Steuer et al. |

(Continued)

FOREIGN PATENT DOCUMENTS

| | | |
|---|---|---|
| EP | 1184663 | 3/2002 |
| FR | 2710517 | 4/1995 |

(Continued)

OTHER PUBLICATIONS

Raaijmakers, Esther et al. "The Inaccuracy of Kubicek's One-Cylinder Model in Thoracic Impedance Cardiography" IEEE Transactions on Biomedical Engineering. vol. 44, No. 1, Jan. 1997.*

(Continued)

*Primary Examiner* — Max Hindenburg
(74) *Attorney, Agent, or Firm* — Fletcher Yoder (57) ABSTRACT

A sensor assembly and/or systems for bioimpedance measurements may provide information related to the lean body water of the patient's tissue. The information related to the patient's lean body water may be determined by spectroscopic methods for determining water fraction. The patient's fat-free hydration levels may be incorporated into determinations of physiological parameters that may be determined by bioimpedance, such as cardiac output, hemtocrit, or body fat percentage.

23 Claims, 4 Drawing Sheets

U.S. PATENT DOCUMENTS

| | | | |
|---|---|---|---|
| 5,615,689 A | 4/1997 | Kotler | |
| 5,687,721 A | 11/1997 | Kuhls | |
| 5,701,902 A | 12/1997 | Vari et al. | |
| 5,720,284 A | 2/1998 | Aoyagi et al. | |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,833,602 A | 11/1998 | Osemwota | |
| 5,853,364 A | 12/1998 | Baker, Jr. et al. | |
| 5,860,919 A | 1/1999 | Kiani-Azarbayjany et al. | |
| 5,906,582 A | 5/1999 | Kondo et al. | |
| 6,064,898 A | 5/2000 | Aldrich | |
| 6,125,297 A | 9/2000 | Siconolfi | |
| 6,149,591 A | 11/2000 | Henderson et al. | |
| 6,178,342 B1 | 1/2001 | Thompson et al. | |
| 6,222,189 B1 | 4/2001 | Misner et al. | |
| 6,246,894 B1 | 6/2001 | Steuer et al. | |
| 6,280,396 B1 | 8/2001 | Clark et al. | |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,442,408 B1 | 8/2002 | Wenzel et al. | |
| 6,466,807 B1 | 10/2002 | Dobson et al. | |
| 6,488,677 B1 | 12/2002 | Bowman et al. | |
| 6,512,936 B1 | 1/2003 | Monfre et al. | |
| 6,561,986 B2 | 5/2003 | Baura | |
| 6,591,122 B2 | 7/2003 | Schmitt | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 | 9/2003 | Aldrich | |
| 6,635,491 B1 | 10/2003 | Khalil et al. | |
| 6,636,759 B2 | 10/2003 | Robinson | |
| 6,643,543 B2 | 11/2003 | Takehara et al. | |
| 6,654,620 B2 | 11/2003 | Wu et al. | |
| 6,668,181 B2 | 12/2003 | Wenzel et al. | |
| 6,675,029 B2 | 1/2004 | Monfre et al. | |
| 6,687,519 B2 | 2/2004 | Steuer et al. | |
| 6,777,240 B2 | 8/2004 | Hazen et al. | |
| 6,849,046 B1 | 2/2005 | Eyal-Bickels | |
| 6,950,699 B1 | 9/2005 | Manwaring et al. | |
| 7,043,293 B1 | 5/2006 | Baura | |
| 7,054,453 B2 | 5/2006 | Causevic | |
| 7,181,264 B2 | 2/2007 | Wiesmann et al. | |
| 7,236,811 B2 | 6/2007 | Schmitt | |
| 7,239,902 B2* | 7/2007 | Schmitt et al. | 600/310 |
| 7,246,620 B2 | 7/2007 | Conroy, Jr. | |
| 7,277,741 B2 | 10/2007 | Debreczeny et al. | |
| 7,383,105 B2 | 6/2008 | Conroy, Jr. | |
| 7,826,890 B1* | 11/2010 | Winchester et al. | 600/477 |
| 2001/0020122 A1 | 9/2001 | Steuer et al. | |
| 2003/0060693 A1 | 3/2003 | Monfre et al. | |
| 2004/0116969 A1* | 6/2004 | Owen et al. | 607/6 |
| 2004/0127777 A1 | 7/2004 | Richti et al. | |
| 2004/0147034 A1 | 7/2004 | Gore et al. | |
| 2004/0230106 A1 | 11/2004 | Schmitt et al. | |
| 2005/0065484 A1 | 3/2005 | Watson | |
| 2005/0113678 A1* | 5/2005 | Villard et al. | 600/425 |
| 2005/0177062 A1* | 8/2005 | Skrabal et al. | 600/547 |
| 2005/0192488 A1* | 9/2005 | Bryenton et al. | 600/301 |
| 2005/0203429 A1* | 9/2005 | Judy | 600/508 |
| 2005/0283060 A1* | 12/2005 | Pekker et al. | 600/345 |
| 2006/0009710 A1* | 1/2006 | Bernstein | 600/547 |
| 2006/0020181 A1 | 1/2006 | Schmitt | |
| 2006/0058690 A1 | 3/2006 | Bartnik et al. | |
| 2006/0084864 A1 | 4/2006 | Schmitt et al. | |
| 2006/0155193 A1* | 7/2006 | Leonardi et al. | 600/473 |
| 2006/0167350 A1 | 7/2006 | Monfre et al. | |
| 2006/0167363 A1 | 7/2006 | Osypka et al. | |
| 2006/0253016 A1 | 11/2006 | Baker, Jr. et al. | |
| 2006/0276696 A1 | 12/2006 | Schurman | |
| 2006/0287603 A1 | 12/2006 | Bartnik et al. | |
| 2007/0062531 A1 | 3/2007 | Fisher et al. | |
| 2007/0078312 A1* | 4/2007 | Fine et al. | 600/316 |
| 2007/0106137 A1 | 5/2007 | Baker, Jr. et al. | |
| 2007/0118027 A1 | 5/2007 | Baker, Jr. et al. | |
| 2007/0129614 A1 | 6/2007 | Schmitt et al. | |
| 2007/0179386 A1 | 8/2007 | Michard et al. | |
| 2007/0197859 A1 | 8/2007 | Schaer et al. | |
| 2008/0009690 A1 | 1/2008 | Debreczeny et al. | |
| 2008/0015451 A1 | 1/2008 | Hatib et al. | |
| 2008/0033305 A1 | 2/2008 | Hatib et al. | |
| 2008/0045832 A1 | 2/2008 | Mcgrath | |
| 2008/0076983 A1 | 3/2008 | Debreczeny et al. | |
| 2008/0077023 A1 | 3/2008 | Campbell et al. | |
| 2008/0081975 A1 | 4/2008 | Agashe et al. | |
| 2008/0097173 A1 | 4/2008 | Soyemi et al. | |
| 2008/0146906 A1 | 6/2008 | Baker, Jr. et al. | |
| 2008/0220512 A1 | 9/2008 | Koh et al. | |
| 2008/0221406 A1 | 9/2008 | Baker, Jr. | |
| 2008/0221407 A1 | 9/2008 | Baker, Jr. | |
| 2008/0221409 A1 | 9/2008 | Hoarau | |
| 2008/0221410 A1 | 9/2008 | Campbell et al. | |
| 2008/0221411 A1 | 9/2008 | Hausmann et al. | |
| 2008/0221412 A1 | 9/2008 | Baker, Jr. et al. | |
| 2008/0221414 A1 | 9/2008 | Baker, Jr. | |
| 2008/0221416 A1 | 9/2008 | Baker, Jr. | |
| 2008/0275317 A1 | 11/2008 | Cho et al. | |
| 2009/0076345 A1* | 3/2009 | Manicka et al. | 600/301 |
| 2009/0216096 A1 | 8/2009 | Bloom et al. | |

FOREIGN PATENT DOCUMENTS

| | | |
|---|---|---|
| JP | 11244266 | 9/1999 |
| JP | 2004081427 | 3/2004 |
| WO | WO9313706 | 7/1993 |
| WO | WO9519562 | 7/1995 |
| WO | WO9834097 | 8/1998 |
| WO | WO9953834 | 10/1999 |
| WO | WO0071025 | 11/2000 |
| WO | WO0116577 | 3/2001 |
| WO | WO03010510 | 2/2003 |
| WO | WO2005025448 | 3/2005 |
| WO | WO2005041765 | 5/2005 |

OTHER PUBLICATIONS

Heimsch, Werner et al. "Left Ventricular Volume Measurement by the Conductance Catheter and Variations in the Hematocrit in Small Animals" Cardiovascular Engineering (2007) 7:43-46.*

Buijs, K., et al., "Near-Infrared Studies of the Structure of Water. I. Pure Water," *The Journal of Chemical Physics*, vol. 39, No. 8, pp. 2035-2041 (Oct. 15, 1963).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol. Res.*, vol. 277, pp. 489-495 (1985).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Bommannan, D., et al., "Examination of Stratum Corneum Barrier Function In Vivo by Infrared Spectroscopy," *J. Invest Dermatol*, vol. 95, pp. 403-408 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Martin, K., "Direct Measurement of Moisture in Skin by NIR spectroscopy," *J. Soc. Cosmet. Chem.*, 44:249-261 (1993).

Matcher, S. J., et al., "Absolute quantification of deoxyhaemoglobin concentration in tissue near infrared spectroscopy," *Phys. Med. Biol.*, vol. 39, pp. 1295-1312 (1994).

Takeo, T. et al., "Skin Hydration State Estimation Using a Fiber-Optic Refractometer," *Applied Optics*, vol. 33, No. 19, Jul. 1994, p. 4267-72.

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Kumar, Gitesh, et al., "Non-Invasive Optical Assessment of Tissue Hydration," *International conference on Biomedical Engineering*, Jun. 3-5, 1996, Hong Kong, pp. C2-5.

Schmitt et al., *Proc. SPIE*, "Optimum wavelengths for measurement of blood hemoglobin content and tissue hydration by NIR spectrophotometry," 2678:442-453 (1996).

Martin, Kathleen, "In Vivo Measurements of Water in Skin by Near-Infrared Reflectance," *Applied Spectroscopy*, vol. 52, No. 7, 1998, pp. 1001-1007.

Stranc, M.F., et al., "Assessment of tissue viability using near-infrared spectroscopy," *British Journal of Plastic Surgery*, vol. 51, pp. 210-217, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Fornetti, Willa C., et al., "Reliability and validity of body composition measures in female athletes," Journal of Applied Physiology, vol. 87, pp. 1114-1122, (1999).

Kalantar-Zadeh, Kamyar, et al., "Near infra-red interactance for nutritional assessment of dialysis patients," *Nephrol Dial Transplant*, vol. 14, pp. 169-175 (1999).

Sowa et al., "New-infrared spectroscopic assessment of tissue hydration following surgery", *Journal of Surgical Research*, 86:62-69 (1999).

Lucassen, G., et al., "Water Content and Water Profiles in Skin Measured by FTIR and Raman Spectroscopy," *Proc. SPIE*, vol. 4162, pp. 39-45 (2000).

Attas, Michael, et al., "Visualization of cutaneous hemoglobin oxygenation and skin hydration using near-infrared spectroscopic imaging," *Skin Research and Technology*, vol. 7, pp. 238-245, (2001).

Du, Y., et al., "Optical properties of porcine skin dermis between 900 nm and 1500 nm," *Phys. Med. Biol.*, vol. 46, pp. 167-181 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Lever, M., et al., "Some ways of looking at compensatory kosmotropes and different water environments," *Comparative Biochemistry and Physiolog.*, vol. 130, Part A, pp. 471-486, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Bouwstra, Joke A., et al., "Water Distribution and Related Morphology in Human Stratum Corneum at Different Hydration Levels," *J. Invest Dermatol*, vol. 150, pp. 750-758 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Arimoto et al., "Non-contact skin moisture measurement based on near-infrared spectroscopy", *Applied Spectroscopy*, 58(12):1439-1445 (2004).

Yamakoshi, K.. et al.; "Electrical admittance cuff for non-invasive and simultaneous measurement of hematocrit, arterial pressure and elasticity using volume-oscillometric method," *Med. & Biol. Eng. & Comput.*,; pp. S99-S107; Jul. 1994.

Yamakoshi, K. et al.; "Noninvasive Measurement of Hematocrit by Electrical Admittance Plethysmography Technique," *IEEE Transactions on Biomedical Engineering*, vol. BME-27, No. 3; pp. 156-161; Mar. 1980.

Yamakoshi, K., et al. "Noninvasive Measurement of Hematocrit by Electrical Admittance Plethysmography Technique"; IEEE Transactions on Biomedical Engineering, vol. BME-27, No. 3, pp. 156-161 (Mar. 1980).

Yamakoshi, K., et al. "Electrical admittance cuff for non-invasive and simultaneous measurement of haematocrit, arterial pressure and elasticity using volume-oscillometric method"; Med. & Biol. Eng. & Comput., 32, S99-S107 (1994).

\* cited by examiner

BIOIMPEDANCE SYSTEM AND SENSOR AND TECHNIQUE FOR USING THE SAME

BACKGROUND

The present disclosure relates generally to medical devices and, more particularly, to sensors and systems for measuring physiological parameters of a patient.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

In some instances, physicians may wish to have information about the condition and state of internal organs such as the heart. Cardiac activity may be assessed by a variety of methods, including echocardiography, which may be used for measuring stroke force, inotropism, contractility and ejection fraction. In addition, the amount of blood a heart ejects in one heartbeat, stroke volume and other hemodynamic parameters are frequently determined. An additional parameter, cardiac output (i.e., cardiac output per minute) may also be determined. From these parameters, a general determination of cardiac function may be derived, which in turn is a basis for the diagnosis of heart diseases and other clinical conditions.

Because patients in hospital settings may experience sudden changes in heart condition, it may be advantageous to collect cardiac data continuously to more quickly respond to such changes. However, some techniques for determining cardiac function may not be suitable for long-term continuous monitoring of a patient. For example, echocardiography is not really appropriate for monitoring patients with serious heart diseases in ICUs because it involves the constant attention of medical personnel.

One existing technique for determining cardiac function which has been developed is known as impedance cardiography. Impedance cardiography involves measuring the electrical impedance of a subjects body using a series of electrodes placed on the skin surface. Changes in electrical impedance at the body's surface are used to determine changes in tissue volume that are associated with the cardiac cycle, and accordingly, measurements of cardiac output and other cardiac function. Such impedance-based techniques, however, may be relatively inaccurate in calculating certain hemodynamic parameters, such as stroke volume, for certain patients.

BRIEF DESCRIPTION OF THE DRAWINGS

Advantages of the disclosure may become apparent upon reading the following detailed description and upon reference to the drawings in which.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

According to various embodiments, sensors and monitoring systems are provided herein that may employ bioimpedance measurements in combination with measurements of tissue water fraction to more accurately determine physiological parameters such as cardiac output, hematocrit, and/or body weight. Bioimpedance is often determined according to an equation that relies upon certain assumptions for a "typical" human body. These assumptions may not hold true for all patients, which may lead to errors in the calculation of stroke volume and other hemodynamic parameters as well as of cardiac output.

Bioimpedance devices pass a low level electrical current through a patient's body to measure the impedance or resistance of the tissue to the flow of electricity. The higher the amount of water in the body, the less resistance there is to the electrical current. The estimation of bioelectrical impedance parameters may be based on certain assumptions that, for example, the electrical current follows the path of least resistance through the body and that both the body and its various segments conform to a 'typical' cylindrical shape. In addition, most standard bioimpedance determinations may introduce error by assuming a constant or "typical" hydration level of the patient. However, because measurement of resistance is affected markedly by the level of hydration of the patient, dehydration from such sources as clinical condition, heat exposure, exercise or alcohol consumption can affect the calculated values of any physiological parameter determined by bioimpedance.

More specifically, the impedance of a patient's tissue may be related to the resistance of the tissues, which is proportional to the fluid volume, and the reactance, which is inversely proportional to the capacitance of the cell membranes, tissue interface, and nonionic tissues. Both the resistance of the reactance of a patient's tissue may be impacted by tissue hydration. Human body hydration may be determined using spectroscopic techniques such as near infrared spectroscopy. By measuring a tissue water fraction, the hydration level of the skin may be determined, which in turn is correlated to the lean body water content of the human body. By incorporating a measurement of lean body water to provide a correction factor to standard bioimpedance calculations, variations in tissue hydration may be accounted for. The use of spectrophotometric devices in combination with bioimpedance sensing provides the advantage of early detection, allowing for proper treatment and preventative measures to be taken to assist in normalizing a patient's condition. Additionally, both bioimpedance and spectrophotometric devices are non-invasive, which provides an advantage related to ease of use.

Figure 1:
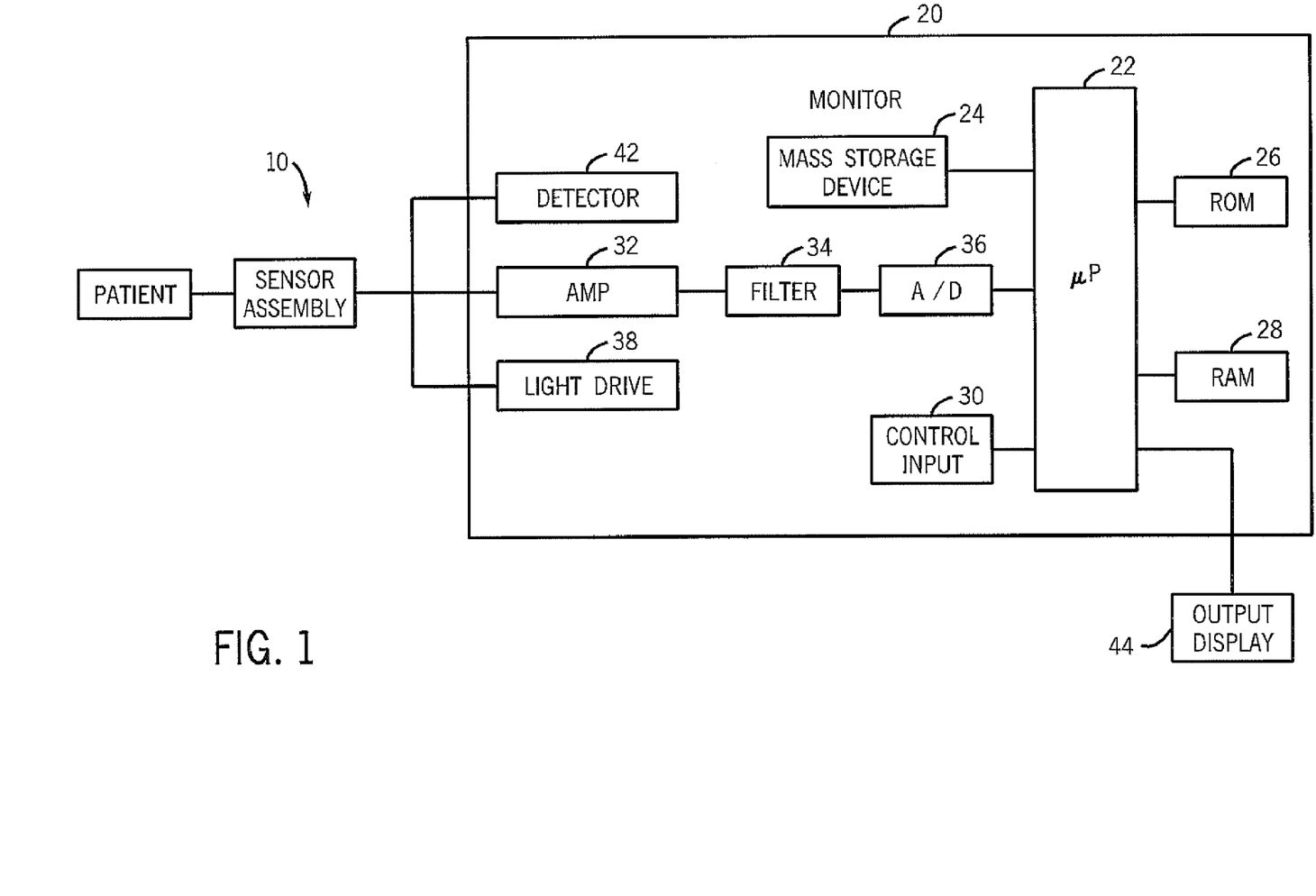
FIG. 1 illustrates a block diagram of a monitoring system in accordance with an exemplary embodiment.

FIG. 1 illustrates a block diagram implementing a monitoring system in accordance with an exemplary embodiment. The system includes a sensor assembly 10. The sensor assembly 10 is capable of providing a signal related to the patient bioimpedance to a monitor 20. The monitor 20 has a microprocessor 22 that is, in turn, capable of calculating various parameters related to bioimpedance, including cardiac output, hematocrit, and/or body fat percentage. In addition, the sensor assembly 10 is capable of providing a fluid parameter signal related to a patient's tissue water content to the monitor 20. The microprocessor 22 is also capable of calculating fluid parameters using appropriate algorithms. In certain embodiments, the fluid parameter information contained in the signal from the sensor assembly 10 is processed to provide additional input and/or correction factors to the calculation of the bioimpedance calculations.

The microprocessor 22 is coupled to other component parts of the monitor 20, such as a mass storage device 24, a ROM 26, a RAM 28, and control inputs 30. The mass storage device 24, the ROM 26, and/or the RAM 28 may hold the algorithms or routines used to determine the bioimpedance parameters and/or the fluid levels or metrics and may store the data collected by the sensor assembly 10 for use in the algorithms. The mass storage device 24 may be any suitable device such as a solid state storage device, an optical medium such as an optical disk, or a magnetic medium such as a hard disk. The monitor 20 may include a display 44 for providing information to healthcare providers related to the bioimpedance and/or fluid parameter determinations of the microprocessor 22.

Detected signals are passed from the sensor assembly 10 to the monitor 20 for processing. In the monitor 20, the signals may be amplified and filtered by amplifier 32 and filter 34, respectively, before being converted to digital signals by an analog-to-digital converter 36. The digitized signals may then be used to determine the fluid parameters and/or may be stored in RAM 28. A light drive unit 38 in the monitor 20 controls the timing of the optical components, such as emitters, in the sensor assembly 10. Additionally, the monitor 20 may include a circuit for generating current to electrode components of the sensor assembly 10.

In an embodiment, the emitters are manufactured to operate at one or more certain wavelengths. Variances in the wavelengths actually emitted may occur which may result in inaccurate readings. To help avoid inaccurate readings, the sensor assembly 10 may include components such as an encoder that may be used to calibrate the monitor 20 to the actual wavelengths being used. The encoder may be a resistor, for example, whose value corresponds to coefficients stored in the monitor 20. The coefficients may then be used in the algorithms. Alternatively, the encoder may also be a memory device, such as an EPROM, that stores information, such as the coefficients themselves. Once the coefficients are determined by the monitor 20, they may be inserted into algorithms for determining bioimpedance and/or water fraction in order to calibrate the system to particular optical components. In an embodiment in which the sensor assembly 10 includes a multiple-wavelength water fraction sensor, a set of coefficients chosen for any set of wavelength spectra may be determined by a value indicated by the encoder corresponding to a particular light source in a particular sensor assembly 10. In one embodiment, multiple resistor values may be assigned to select different sets of coefficients. In another embodiment, the same resistors are used to select from among the coefficients different sources.

Control inputs 30 may allow a user to interface with the monitor 20. Control inputs 30 may be, for instance, a switch on the monitor 20, a keyboard or keypad, or a port providing instructions from a remote host computer. For example, a sensor assembly 10 may include a variable number of water fraction sensors and bioimpedance sensors. The monitor 20 may receive user inputs related to the configuration and number of such sensors on the patient. Additionally, patient data may be entered, such as sex, weight, age and medical history data, including, for example, whether a patient suffers from emphysema, psoriasis, etc. This information may be used to validate certain baseline bioimpedance or water fraction measurements or to assist in the understanding of anomalous readings. For example, the skin condition psoriasis may alter the baseline reading of skin water and, therefore, would affect any determination of possible bed sores or other skin wounds.

Figure 2:
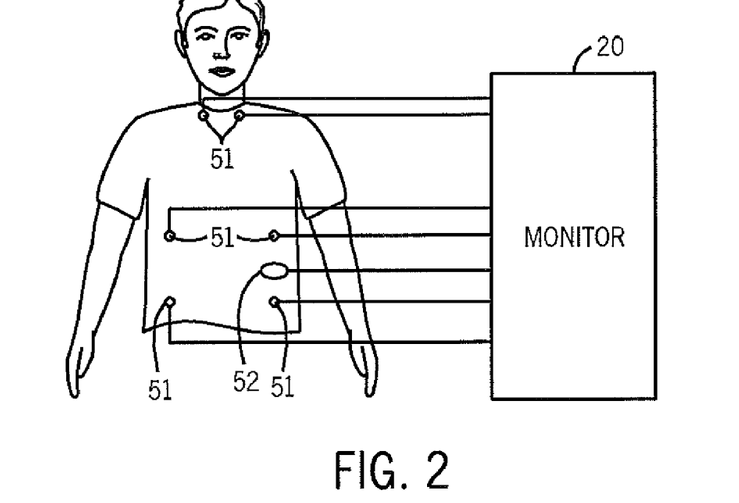
FIG. 2 illustrates perspective view of an exemplary sensor assembly applied to a patient.

An exemplary sensor assembly 10 is shown in FIG. 2 and includes one or more bioimpedance sensors 50, shown here as electrode patches 51, and one or more water fraction sensors 52. Each individual electrode patch 51 and water fraction sensor 52 may be coupled to the monitor 20, either by direct electrical connections or remotely. The electrode patch 51 may be of any suitable type for bioimpedance measurements, such as those offered for sale by Biopac Systems, Inc. (Goleta, Calif.). Each electrode patch 50 may include one or more current source electrodes for applying an electrical current and one or more voltage detection electrodes for detecting the voltage drop of the applied current as a result of the impedance of the tissue. In one embodiment, at least one current source electrode sends a small, high frequency sinusoidal current through the tissue. At least one detecting electrode measures the resulting voltage drop and phase lag of the sinusoidal current that has passed through the tissue. The electrode patch 51 may be of any size or type depending upon the patient, measurement period, and other specifications. In an embodiment, a bioimpedance sensor 50 may also include electrode band sensors. In certain embodiments, the electrode frequency may range from about 1 kHz to about 1000 kHz.

Figure 3:
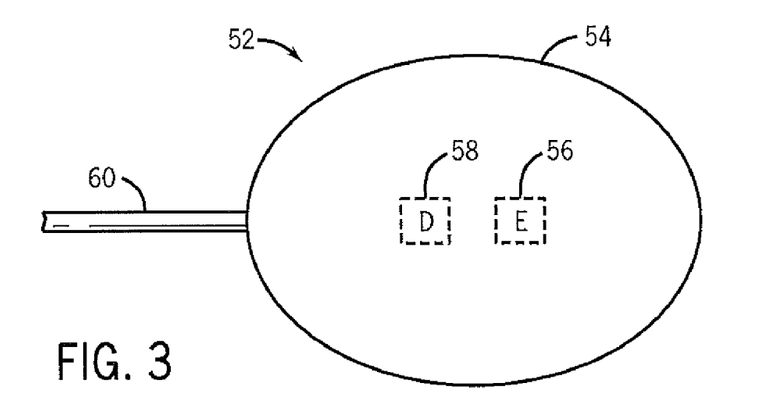
FIG. 3 illustrates a view of an exemplary water fraction sensor that may be used in conjunction with the sensor assembly of FIG. 2.
Figure 4:
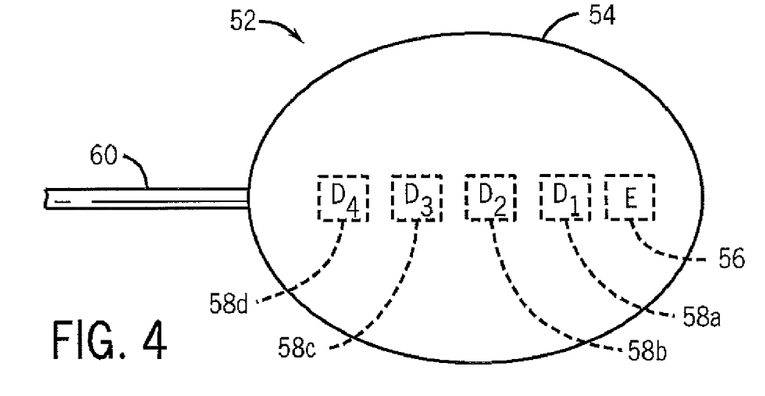
FIG. 4 illustrates an alternative view of an exemplary water fraction sensor that may be used in conjunction with the sensor assembly of FIG. 2.

Illustrations of exemplary water fraction sensors 52 are shown in FIG. 3 and FIG. 4. The sensor 52 may include an emitter 56 configured to transmit electromagnetic radiation, such as light, into the tissue of a patient. The electromagnetic radiation is scattered and absorbed by the various constituents of the patient's tissues, such as water and protein. A photoelectric detector 58 in the sensor 52 is configured to detect the scattered and reflected light and to generate a corresponding electrical signal. The sensor 52 directs the detected signal from the detector 58 to a monitor 20.

Specifically, FIG. 3 illustrates a diagrammatic view of a water fraction sensor 52. The sensor 52 may be a handheld sensor that a caregiver can move around on a patient or may be affixed to a particular location on the patient. The sensor 52 may have a housing 54 having a contoured upper surface to allow a user to easily hold onto the sensor 52. For example, the housing 54 may be similar in size and shape to a computer mouse. The sensor 52 may be communicatively coupled to the monitor 20 via a cable 60. In embodiments, the sensor 52 may employ wireless communication technology to transmit information back to monitor 20, thus eliminating the cable 60. In an embodiment, the sensor 52 may have a substantially flat surface of the sensor housing 54. The emitter 56 and detector 58 are located on this surface to allow them to efficiently couple to the patient's skin during use. An optical coupling gel, transparent talc, or other medium may be used to aid in achieving a proper optical coupling between the emitter 56 and detector 58 and the patient's skin.

The spacing between the emitter 56 and detector 58 may be determined based upon the region of skin or compartment of the body that is to be tested. Generally, for relatively shallow probing, the emitter and detector may be relatively close to one another, while for deeper probing the emitter 56 and detector 58 will be further separated. For example, when diagnosing skin wounds, the emitter 56 and detector 58 may be 1 to 5 mm apart, because the electromagnetic radiation need only penetrate into layers of skin. However, for detecting water fraction in deeper compartment, the emitter 56 and detector 58 may be placed further apart, such as 5 to 15 mm apart, for example, to allow the electromagnetic radiation to penetrate into deeper tissue before being reflected or scattered to the detector 58. In embodiments, somewhat shorter and less strongly absorbed wavelengths may be used in conjunction with longer spacings.

The water fraction sensor 52 includes an emitter 56 and a detector 58 that may be of any suitable type. For example, the emitter 56 may be one or more light emitting diodes adapted to transmit one or more wavelengths of light in the red to infrared range, and the detector 58 may one or more photodetectors selected to receive light in the range or ranges emitted from the emitter 56. Alternatively, an emitter 56 may also be a laser diode or a vertical cavity surface emitting laser (VCSEL). An emitter 56 and detector 58 may also include optical fiber sensing elements. An emitter 56 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a water fraction sensor 52 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. A tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 56, the detector 58 may be disposed on a sensor housing 54, which may be made of any suitable material, such as plastic, foam, woven material, or paper. Alternatively, the emitter 56 and the detector 58 may be remotely located and optically coupled to the sensor assembly 10 using optical fibers.

The water fraction sensor 52 may include a "transmission type" sensor. Transmission type sensors include an emitter 56 and detector 58 that are typically placed on opposing sides of the sensor site. If the sensor site is a fingertip, for example, the sensor assembly 10 is positioned over the patient's fingertip such that the emitter 56 and detector 58 lie on either side of the patient's nail bed. In other words, the sensor assembly 10 is positioned so that the emitter 56 is located on the patient's fingernail and the detector 58 is located 180° opposite the emitter 56 on the patient's finger pad. During operation, the emitter 56 shines one or more wavelengths of light through the patient's fingertip and the light received by the detector 58 is processed to determine various physiological characteristics of the patient. In each of the embodiments discussed herein, it should be understood that the locations of the emitter 56 and the detector 58 may be exchanged. For example, the detector 58 may be located at the top of the finger and the emitter 56 may be located underneath the finger. In either arrangement, the sensor assembly 10 will perform in substantially the same manner.

Reflectance type sensors, as shown in FIG. 3 and FIG. 4, also operate by emitting light into the tissue and detecting the light that is transmitted and scattered by the tissue. However, reflectance type sensors include an emitter 56 and detector 58 that are typically placed on the same side of the sensor site. For example, a reflectance type sensor may be placed on a patient's fingertip or forehead such that the emitter 56 and detector 58 lie side-by-side. Reflectance type sensors detect light photons that are scattered back to the detector 58. A sensor assembly 10 may also be a "transflectance" sensor, such as a sensor that may subtend a portion of a baby's heel.

Turning to FIG. 4, a water fraction sensor 52 having multiple detectors in accordance with an embodiment is illustrated. The sensor 52 is capable of sensing various depths of tissue because of the multiple detectors 58a-d. Any number of detectors 58a-d may be used, and the more detectors that are used, the higher the resolution. In this example, the sensor 52 has four detectors 58a-d arranged linearly with increasing distance from the emitter 56. The detector 58a, in closest proximity to the emitter 56, is used for sensing in shallow tissue, as the light transmitted from the emitter 56 does not penetrate far into the tissue before arriving back at the detector 58a. In an embodiment, the detector 58d, farthest away from the emitter 56, may be used for sensing deeper tissue because the signals from emitter 56 penetrate deeper into the tissue before arriving at detector 58d than those that arrive at detector 58a. Accordingly, this arrangement allows for the monitor 20 to detect at multiple depths of tissue. In embodiments, similar results may be achieved with a water fraction sensor 52 having a single emitter and detector location with adjustable spacing between them, or a sensor having multiple emitters or emitter locations and a single detector or detector location.

Figure 5:
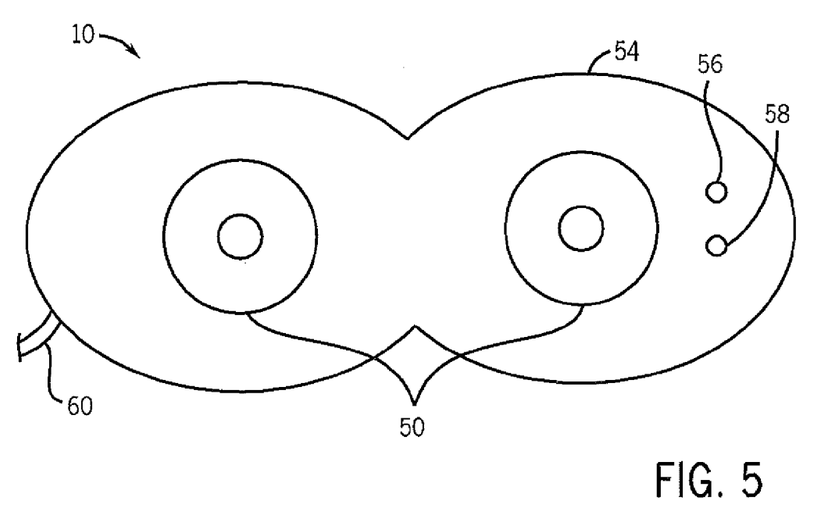
FIG. 5 depicts an exemplary dipole impedance electrode with an integrated water fraction sensor.

FIG. 5 illustrates an embodiment of a sensor assembly 10 in which a single sensor housing 54 includes both a bioimpedance sensor 50 and a water fraction sensor 52. For example, as depicted, the assembly 10 may include a patch-type dipole bioimpedance sensor with two electrodes for sensing the impedance of the tissue. The sensor housing 54 may also include one or more emitters 56 and any suitable number of detectors 58 for use in detecting tissue hydration. Both the bioimpedance sensor 50 and the water fraction optical components 56 and 58 may communicate with the monitor 20 through common cable 60.

Figure 6:
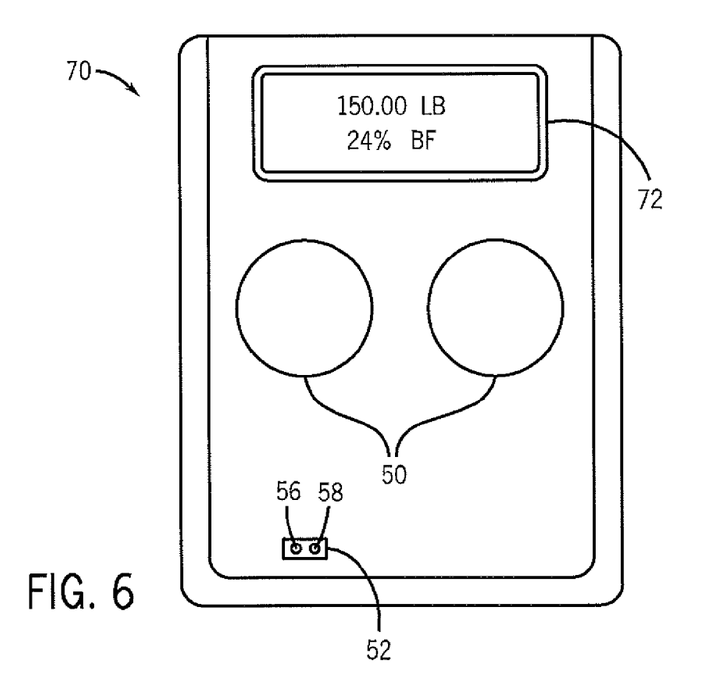
FIG. 6 illustrates a perspective view of a scale that incorporates a water fraction sensor together with a bioimpedance sensor.

FIG. 6 illustrates an embodiment of a scale 70 that may incorporate a bioimpedance sensor and water fraction sensor 52 to determine body fat percentage. A user may step on the scale 70, placing his feet on a suitable arrangement of electrodes of the bioimpedance sensor 50 and the optical components of the water fraction sensor 52. The impedance of the tissue between current and detecting electrodes as well as the detected light at a detector 58 may be incorporated into suitable algorithms, which may be programmed into a processing chip located in the housing of the scale 70, to determine body fat percentage. The results generated by the processing chip may be sent to a display 72 for viewing by the user.

Figure 7:
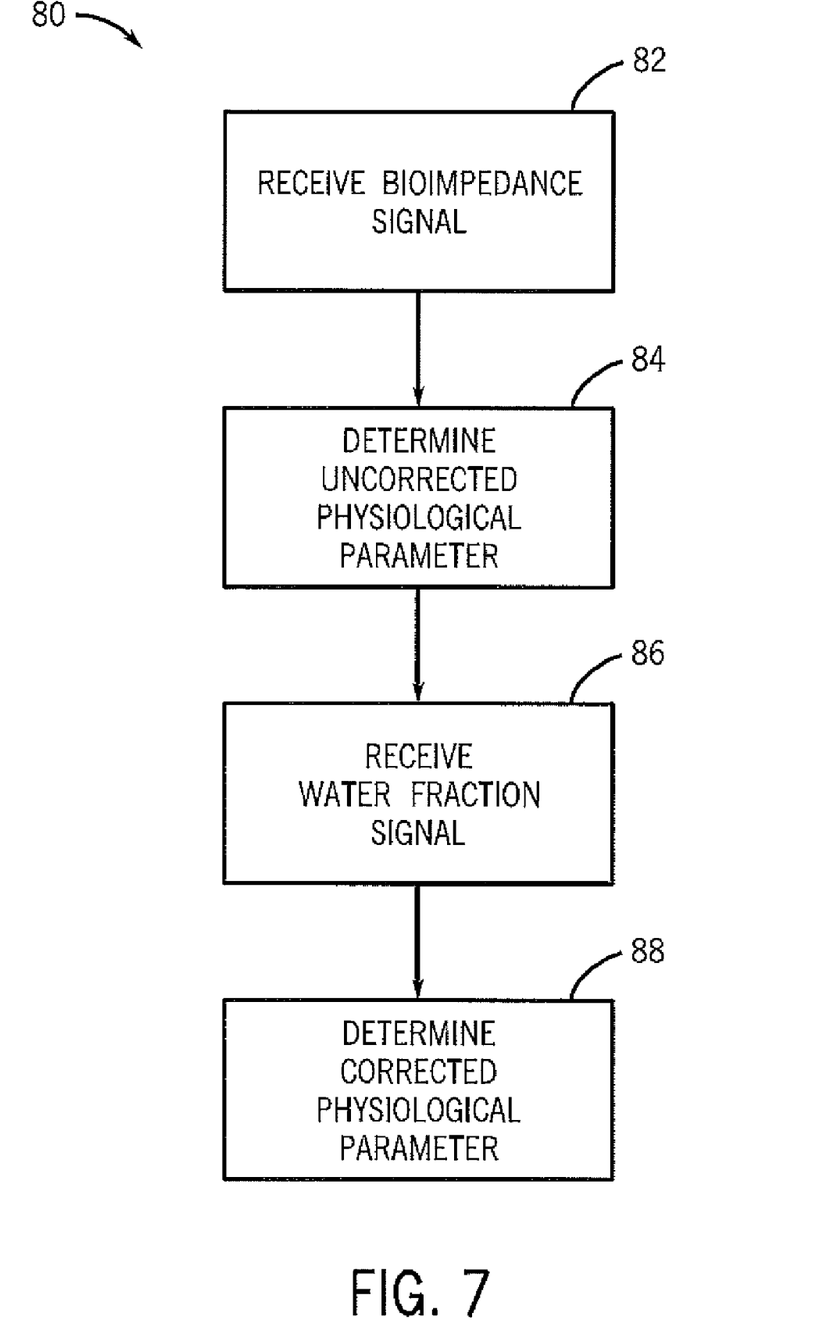
FIG. 7 illustrates a flow chart for correcting bioimpedance measurements based on signals received from a water fraction sensor.

FIG. 7 is a flow chart of an embodiment of a processing method 80. In the embodiment, the impedance of the tissue of a patient may be measured and received by a suitable device, such as a monitor 20 (block 82). Next, the signal may be processed and analyzed to determine a physiological parameter, such as cardiac output or body fat percentage, from the received signal (block 84). In an embodiment, the method may omit step 84 and directly receive both the bioimpedance signal and the water fraction signal to determine the corrected physiological parameter.

The signals sent from the sensor assembly 10 may include a code or other identification parameter that may allow the monitor 20 to select an appropriate software instruction for processing the signal at block 84 or 88. Based on the value of the received signals corresponding to voltage drop across the electrodes, the electrical impedance may be calculated using various algorithms. In an embodiment, impedance Z may be calculated as the ratio of voltage (V) to current (I); i.e., Z=V/I.

In one embodiment, the Kubicek equation, shown as Equation 1, may be used for calculating stroke volume and other hemodynamic parameters from a variation of the impedance signal:

$$SV=R(L/Z\sigma)_2(VET)(dZ/dt_{min}) \quad (1)$$

where R is blood resistivity, L is the distance between the inner voltage sensing electrodes, $Z\sigma$ is the mean thoracic impedance determined from the inner, voltage sensing electrodes, VET is the ventricular ejection time and $dZ/dt_{min}$ is the maximum negative slope change of the time-differentiated impedance signal, which is the time-differentiated difference between the impedances determined at the center two electrodes. Cardiac output per minute is stroke volume times heart rate in beats per minute. In embodiments, the heart rate may be determined from an ECG or a pulse oximetry sensor and/or system. In an embodiment, the received signal from the sensor assembly 10 includes information such as the distance L between the electrodes.

In addition, a memory associated with the monitor 20 may contain comparison charts or tables for comparing measured impedance or measured impedance changes with hemodynamic measurement values. In one embodiment, the processing algorithm may receive the voltage measurement and calculate a numerical indicator of the electrical impedance for display. In one embodiment, an algorithm may use as input electrical impedance data to output a more qualitative metric that correlates to a patient clinical condition.

In one embodiment, hematocrit may be determined by using a mapping function to relate particular values of the voltage measurement to corresponding hematocrit values which may depend on certain physical characteristics of the patient (height, weight, etc.) and certain physical characteristics of the sensor 50. The mapping function may therefore by empirically determined under actual or simulated conditions and expressed as either a continuous or discrete function, the latter being implemented, for example, as a look-up table. Also, the physical configuration of the voltage sensing and excitation current electrodes may be arranged to minimize changes in the bioimpedance measurement signal due to changes in the impedance of the tissues other than blood surrounding the electrodes. If the voltage sensing electrodes are spaced at a suitably close distance, the impedance between them will be almost completely due to the volume of blood surrounding the electrodes. Similarly, if the excitation current electrodes closely straddle the voltage sense electrodes, the current field produced by them will not vary appreciably with changes in the impedance of the surrounding tissues.

In addition to receiving signals related to bioimpedance, the method 80 also includes receiving signals related to patient hydration in (block 86). From a water fraction signal, a patient lean body water content may be determined. Methods and algorithms for determining fluid parameters are disclosed in U.S. Pub. No. 20040230106 to Schmitt et al., which is incorporated herein by reference in its entirety for all purposes. Some fluid parameters that may be calculated include water-to-water and protein, water-to-protein, and water-to-fat. For example, in an exemplary embodiment the water fraction, fw, may be estimated based on the measurement of reflectances, $R(\lambda)$, at three wavelengths ($\lambda 1=1190$ nm, $\lambda 2=1170$ nm and $\lambda 3=1274$ nm) and the empirically chosen calibration constants c0, c1 and c2 according to the equation:

$$fw=c2 \log [R(\lambda 1)/R(\lambda 2)]+c1 \log [R(\lambda 2)/R(\lambda 3)]+c0. \quad (2)$$

In an embodiment, the water fraction, fw, may be estimated based on the measurement of reflectances, $R(\lambda)$, at three wavelengths ($\lambda 1=1710$ nm, $\lambda 2=1730$ nm and $\lambda 3=1740$ nm) and the empirically chosen calibration constants c0 and c1 according to the equation:

$$fw = c_1 \frac{\log[R(\lambda_1)/R(\lambda_2)]}{\mathrm{Log}[R(\lambda_3)/R(\lambda_2)]} + c_0. \quad (3)$$

Total tissue water accuracy better than $+/-0.5\%$ can be achieved using Equation (3), with reflectances measured at the three closely spaced wavelengths. Additional numerical simulations indicate that accurate measurement of the lean tissue water content, fw1, can be accomplished using Equation (3) by combining reflectance measurements at 1125 nm, 1185 nm and 1250 nm.

In an embodiment, the water content as a fraction of fat-free or lean tissue content, fw1, is measured. As discussed above, fat contains very little water so variations in the fractional fat content of the body lead directly to variations in the fractional water content of the body. When averaged across many patients, systemic variations in water content result from the variation in body fat content. In contrast, when fat is excluded from the calculation, the fractional water content in healthy subjects is consistent. Additionally, variations may be further reduced by eliminating the bone mass from the calculations. Therefore, particular embodiments may implement source detector separation (e.g. 1-5 mm), wavelengths of light, and algorithms that relate to a fat-free, bone-free water content.

In an embodiment, the lean water fraction, fw1, may be determined by a linear combination of two wavelengths in the ranges of 1380-1390 nm and 1660-1680 nm:

$$fw1=c2 \log [R(\lambda 2)]+c1 \log [R(\lambda 1)]+c0. \quad (4)$$

Additional wavelengths may be incorporated into this or other calibration models in order to improve calibration accuracy.

In an embodiment, tissue water fraction, fw, is estimated according to the following equation, based on the measurement of reflectances, $R(\lambda)$ at a plurality of wavelengths:

$$fw = \frac{\left[\sum_{n=1}^{N} p_n \log\{R(\lambda_n)\}\right] - \left[\sum_{n=1}^{N} p_n\right]\log\{R(\lambda_{N+1})\}}{\left[\sum_{m=1}^{M} q_m \log\{R(\lambda_m)\}\right] - \left[\sum_{m=1}^{M} q_m\right]\log\{R(\lambda_{M+1})\}}, \quad (5)$$

where pn and qm are calibration coefficients. Equation (5) provides cancellation of scattering variances, especially when the N+1 wavelengths are chosen from within the same band (i.e. 950-1400 nm, 1500-1800 nm, or 2000-2300 nm).

At block 88, the lean body water content is used to correct the bioimpedance measurement by providing a more accurate determination of the patient hydration state. In an embodiment, the lean body water content may be directly substituted for a hydration factor assumption of, for example, the Kubicek method. For example, a common hydration assumption of fat-free mass is 73%. In embodiments, the optically determined lean body water may be substituted for the assumed value of 73%. In an embodiment, the water fraction determination may be combined with the electrical impedance determination to provide a ratio or other metric, which may be compared to a threshold, reference value, or look-up table that has been empirically determined to provide a corrected bioimpedance measurement.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of hemodynamic parameters, but these techniques may also be utilized for the measurement and/or analysis of other physiological parameters by bioimpedance techniques. Rather, the various embodiments may to cover all modifications, equivalents, and alternatives falling within the spirit and scope of the disclosure as defined by the following appended claims

What is claimed is:

1. A monitoring system comprising a processor configured to execute instructions to:
   receive a bioimpedance signal from at least one bioimpedance sensor;
   receive a water fraction signal from at least one optical water fraction sensor;
   determine a tissue hydration based on the water fraction signal; and
   determine a physiological parameter value based on the bioimpedance signal and a correction factor, wherein the correction factor is based on the tissue hydration.

2. The system as set forth in claim 1, wherein the physiological parameter value comprises stroke volume.

3. The system as set forth in claim 1, wherein the water fraction signal is used to determine a hydration factor based on lean body water content.

4. The system as set forth in claim 3, wherein the hydration factor is used as part of an algorithm to determine the physiological parameter value.

5. The system as set forth in claim 3, wherein the hydration factor is compared to one or more values in a stored look-up table to determine the corrected physiological parameter value.

6. The system as set forth in claim 1, comprising a sensor assembly capable of generating the bioimpedance signal and the water fraction signal.

7. A method, comprising:
   receiving a bioimpedance signal from at least one bio-impedance sensor;
   receiving a water fraction signal from at least one optical water fraction sensor;
   determining lean body water content based on the water fraction signal; and
   determining a physiological parameter value based at least in part on the bioimpedance signal and the lean body water content using an algorithm, wherein the lean body water content is used to correct for a hydration assumption in the algorithm; and
   providing an output related to the physiological parameter.

8. The method as set forth in claim 7, wherein determining the physiological parameter comprises determining stroke volume.

9. A patient monitoring system comprising:
   a sensor assembly comprising:
   a plurality of electrodes disposed on a sensor body, wherein at least one of the electrodes is capable of generating a signal related to an impedance of a patient's tissue; and
   a water fraction sensor disposed on the sensor body, wherein the water fraction sensor comprises an emitter capable of emitting light into the patient's tissue and a detector capable of detecting the light; and
   a monitor comprising a processor configured to:
   determine a hydration factor of the patient based on a signal from the water fraction sensor; and
   determine a physiological parameter of the patient based on a signal from the plurality of electrodes using an algorithm, wherein the hydration factor is substituted for a hydration factor assumption of the algorithm.

10. The patient monitoring system as set forth in claim 9, wherein the plurality of electrodes comprise a dipole electrode patch.

11. The patient monitoring system as set forth in claim 9, wherein the emitter is configured to emit at least two different wavelengths of light, wherein a first wavelength of light is between 1380-1390 nm, and a second wavelength is between 1660-1680 nm.

12. The patient monitoring system as set forth in claim 9, wherein the emitter is capable of emitting at least three different wavelengths of light.

13. The patient monitoring system as set forth in claim 9, wherein the emitter and the detector are spaced between about 1 mm and about 5 mm apart on the sensor body.

14. The patient monitoring system as set forth in claim 9, comprising at least a second detector spaced apart from the emitter.

15. The system as set forth in claim 1, wherein the physiological parameter value comprises hematocrit.

16. The system as set forth in claim 1, wherein the physiological parameter value comprises body weight.

17. The system as set forth in claim 4, wherein the hydration factor is substituted for a hydration factor assumption of the algorithm prior to the calculation of the physiological parameter.

18. The method as set forth in claim 7, wherein determining the physiological parameter value comprises determining hematocrit, body weight, or both.

19. The patient monitoring system as set forth in claim 9, wherein the algorithm comprises calculating hemodynamic properties using Kubicek's equation, wherein Kubicek's equation comprises:

$$SV = R(L/Z\sigma)_2(VET)(dZ/dt_{min}),$$

wherein SV is a stroke volume, R is a blood resistivity, L is a distance between the plurality of electrodes, $Z\sigma$ is a mean thoracic impedance determined from the plurality of electrodes, VET is a ventricular ejection time, and $dZ/dt_{min}$ is a maximum negative slope change of a time-differentiated impedance signal.

20. The patient monitoring system as set forth in claim 12, wherein a first wavelength is between approximately 950-1400 nm, a second wavelength is between approximately 1500-1800 nm, and a third wavelength between approximately 2000-2300 nm.

21. The patient monitoring system as set forth in claim 12, wherein a first wavelength is approximately 1125 nm, a second wavelength is approximately 1185 nm, and a third wavelength is approximately 1250 nm.

22. The patient monitoring system as set forth in claim 12, wherein a first wavelength is approximately 1190 nm, a second wavelength is approximately 1170 nm, and a third wavelength is approximately 1274 nm.

23. The patient monitoring system as set forth in claim 12, wherein each of a first, second, and third wavelength is selected from the wavelength range between approximately 1710-1740 nm.

* * * * *